US012577237B2

(12) United States Patent
Recsei et al.

(10) Patent No.: US 12,577,237 B2
(45) Date of Patent: Mar. 17, 2026

(54) PROCESS AND INTERMEDIATES FOR THE PREPARATION OF PYROXASULFONE

(71) Applicant: ADAMA AGAN LTD., Ashdod (IL)

(72) Inventors: Carl Recsei, Tel Aviv-Jaffa (IL); Yaniv Barda, Rehovot (IL)

(73) Assignee: ADAMA AGAN LTD. (IL)

( * ) Notice: Subject to any disclaimer, the term of this patent is extended or adjusted under 35 U.S.C. 154(b) by 731 days.

(21) Appl. No.: 17/909,011

(22) PCT Filed: Mar. 4, 2021

(86) PCT No.: PCT/IL2021/050240
§ 371 (c)(1),
(2) Date: Sep. 2, 2022

(87) PCT Pub. No.: WO2021/176456
PCT Pub. Date: Sep. 10, 2021

(65) Prior Publication Data

US 2023/0303546 A1 Sep. 28, 2023

Related U.S. Application Data

(60) Provisional application No. 62/985,364, filed on Mar. 5, 2020.

(51) Int. Cl.
*C07D 413/12* (2006.01)

(52) U.S. Cl.
CPC .................................. *C07D 413/12* (2013.01)

(58) Field of Classification Search
CPC .................................................... C07D 413/12
See application file for complete search history.

(56) References Cited

U.S. PATENT DOCUMENTS

| | | | |
|---|---|---|---|
| 7,488,831 | B2 | 2/2009 | Uchida |
| 2004/0110749 | A1 | 6/2004 | Nakatani et al. |
| 2012/0264947 | A1 | 10/2012 | Frasetto |

FOREIGN PATENT DOCUMENTS

| | | | | |
|---|---|---|---|---|
| EP | 1541561 | A1 | | 6/2005 |
| EP | 1829868 | A1 | † | 9/2007 |
| JP | 2008-290985 | A | † | 12/2008 |
| WO | 2002062770 | A1 | | 8/2002 |
| WO | 2004013106 | A1 | | 2/2004 |
| WO | 2005095352 | A1 | | 10/2005 |
| WO | 2006068092 | A1 | | 6/2006 |
| WO | WO2011/063842 | A1 | † | 6/2011 |

OTHER PUBLICATIONS

Nozaki, K., et al., "Reduction of Sulfoxides by Thioformamizium Salts", Phosphorus and Sulfur and the Related Elements, 22(1), pp. 131-133. (1985), Published online: Dec. 13, 2006 doi: 10.1080/03086648508073362. 4 pgs.

International Search Report for Application No. PCT/IL2021/050240 mailed Jul. 14, 2021. 3 pgs.

"Reduction of Sulloxides by Thioformamizium Salts" Phosphorus and Sulfur and the Related Elements (1985), 22(1), pp. 131-133 Publication Date: Dec. 13, 2006 Inventors: Kenji Nozaki et al.†

† cited by third party

*Primary Examiner* — Kamal A Saeed
(74) *Attorney, Agent, or Firm* — Lerner David LLP

(57) ABSTRACT

The invention relates to a process for preparing a key intermediate of Formula (I) in the synthesis of pyroxasulfone. The process comprises reacting an isoxazole of Formula (II) with a thionating reagent to create an S-substituted thioisoxazole of Formula (III); and combining the S-substituted thioisoxazole of Formula (III) with a pyrazole of the Formula (IV) by introducing a methylene bridge, to obtain a compound of Formula (I). The invention also relates to novel S-substituted thioisoxazole of Formula (III) and processes of preparation thereof, wherein L is halogen or an anionic residue derived from an acid; R is an organic residue derived from a suitable thionating reagent: dimethyl thioformamide, thiosulfate salts, dithiooxamide, alkyl xanthate salts, thiobenzamide, V-substituted thiourea and thioacetate salts.

1 Claim, No Drawings

PROCESS AND INTERMEDIATES FOR THE PREPARATION OF PYROXASULFONE

CROSS-REFERENCE TO RELATED APPLICATIONS

The present application is a national phase entry under 35 U.S.C. § 371 of International Application No. PCT/IL2021/050240 filed Mar. 4, 2021, which claims priority from U.S. Provisional Patent Application No. 62/985,364 filed on Mar. 5, 2020, all of which are incorporated herein by reference.

TECHNICAL FIELD OF THE INVENTION

The present invention relates to a process for producing novel intermediates for the preparation of pyroxasulfone. The present invention further relates to novel S-substituted thioisoxazole derivatives of the general Formula (III).

FIELD AND BACKGROUND OF THE INVENTION

Pyroxasulfone, having the chemical name 3-(5-(difluoromethoxy)-1-methyl-3-(trifluoromethyl)-1H-pyrazol-4-yl] methanesulfonyl)-5,5-dimethyl-4,5-dihydro-1,2-oxazole, has the following structural Formula (1):

(1)

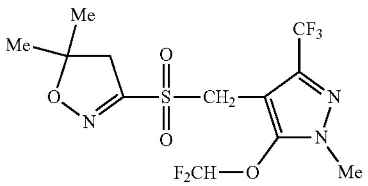

Pyroxasulfone belongs to the class of 3-([(hetero) aryl] methanesulfonyl)-4,5-dihydro-1,2-oxazoles and is used as a herbicide, in particular for pre-emergence control of annual grasses and some broad-leaved weeds in maize, soy beans, wheat and other crops. Pyroxasulfone's mode of action affects apical meristems and coleoptile development and inhibits the biosynthesis of very-long-chain fatty acids in plants with excellent herbicidal activity against grass and broadleaf weeds at lower application rates compared with other commercial herbicides. In fields of genetically modified crops, Pyroxasulfone controlled weeds were resistant to non-selective herbicides. Pyroxasulfone has been classified in the Herbicide Resistance Action Committee Group K3.

Pyroxasulfone is first disclosed by Kumiai Chemical Industry Co., Ltd. and Ihara Chemical Industry Co., Ltd. in WO 2002/062770. It is available on the marketplace as water dispersible granule and suspension concentrate.

Pyroxasulfone's method of preparation was described in several patent applications namely WO 2006/068092 in the name of Ihara, WO 2004/013106 in the name of Kumiai and Ihara and WO 2005/095352 in the name of Ihara.

A typical intermediate for pyroxasulfone synthesis is a (4,5-dihydroisoxazol-3-yl)thiocarboxamidine salt compound of the Formula (2) (e.g. publication WO 2006/068092 in the name of Ihara):

(2)

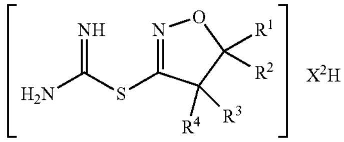

wherein each of $R^1$ and $R^2$ which are independent of each other, is a hydrogen atom, an alkyl group or a cycloalkyl group, each of $R^3$ and $R^4$ which are independent of each other, is a hydrogen atom or an alkyl group, provided that $R^1$ and $R^2$, or $R^2$ and $R^3$, may be bonded to each other to form a cycloalkyl group together with the carbon atoms to which they are bonded, and $X^2$ is a halogen or an anionic residue derived from an acid.

Additional typical intermediate for pyroxasulfone synthesis is a pyrazole derivative represented by the general Formula (3) or a salt thereof (e.g. publication WO 2004/013106 in the name of Kumiai and Ihara):

(3)

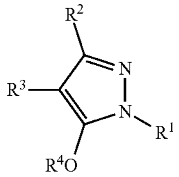

wherein $R^1$ represents a $C_1$ to $C_6$ alkyl group, $R^2$ represents a $C_1$ to $C_3$ haloalkyl group, $R^3$ represents a hydrogen atom or a $C_1$ to $C_3$ alkyl group which may be substituted with one or more substituents selected from the following substituent group a, or a formyl group, $R^4$ represents a hydrogen atom or a $C_1$ to $C_3$ haloalkyl group, provided that $R^4$ represents a $C_1$ to $C_3$ haloalkyl group in the case that $R^3$ is a hydrogen or a formyl group and $R^4$ is a hydrogen group or a $C_1$ to $C_3$ haloalkyl group in the case that $R^3$ is a $C_1$ to $C_3$ alkyl group which may be substituted with one or more substituents selected from the following substituent group a; "Substituent group a" halogen atoms, —SH group, —SC(=NH)$NH_2$ group.

By combining said isoxazole salt of the general Formula (2) with a pyrazole of the general Formula (3), followed by an oxidation, Pyroxasulfone is achieved.

In WO 2004/013106 (≡EP 1541561), where thiourea was used to incorporate a sulfide functionality into the molecule, a reaction of thiourea with 4-bromomethyl-5-difluoromethoxy-1-methyl-3-trifluoromethyl-1H-pyrazole led to the displacement of the bromine, and formation of 2-(5-difluoromethoxy-1-methyl-3-trifluoromethyl-1H-pyrazole-4-ylmethyl)-isothiourea, in the form of its hydrobromide salt (Example 10 of EP 1541561). In turn, this salt was combined with 3-chloro-5,5-dimethyl-2-isoxazoline in the presence of a base, to afford a fluorinated-sulfide of Formula (I) on the pyrazole moiety (Reference Example 1 of EP 1541561).

As can be seen from the chemical structure depicted above, the sulfide of Formula (I) consists of two key fragments, the thioisoxazole and pyrazole rings, linked together by —$CH_2$— (e.g. methylene) bridge.

Thiourea is the prototypical sulfur compound for such a reaction, but this compound has many drawbacks. The thiourea salt is generally prepared in acetonitrile, which is removed in vacuo and the salt obtained by trituration with a different solvent. Finally, it is dissolved in water for reaction with formaldehyde and the pyrazole of the general Formula (3). Direct use of the solution obtained by mixing thiourea and an isoxazole derivative in acetonitrile, suffers from attenuated yields with respect to the use of an isolated salt as well as inhibition of product crystallization. Storage of the thiourea salt requires protection from moisture.

The present invention discloses novel intermediates for producing pyroxasulfone.

SUMMARY OF THE INVENTION

The present invention provides a process for preparing a compound of the Formula (I)

(I)

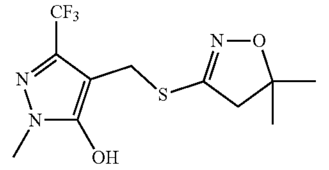

which comprises the following steps:

i) reacting an isoxazole of Formula (II) with a thionating reagent to create an S-substituted thioisoxazole of Formula (III);

ii) combining the S-substituted thioisoxazole of Formula (III) with a pyrazole of the Formula (IV) by introducing a methylene bridge, to obtain a compound of Formula (I)

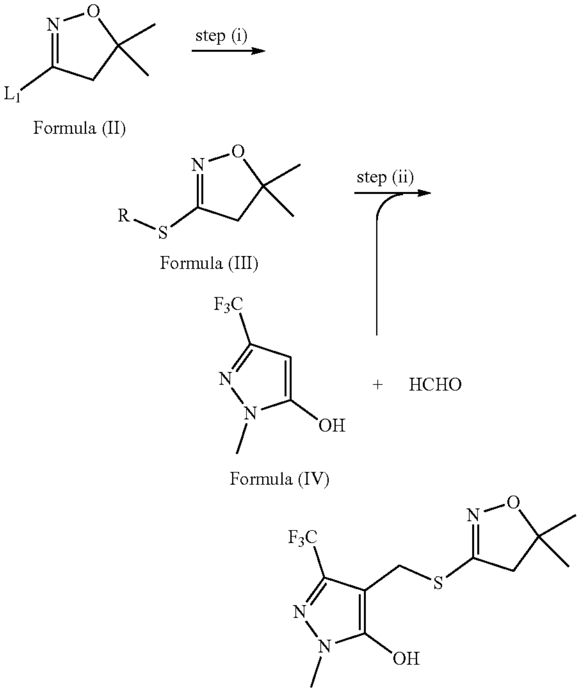

Formula (I)

wherein $L_1$ is a leaving group; R is an organic residue derived from a suitable thionating reagent: dimethyl thioformamide, thiosulfate salts, dithiooxamide, alkyl xanthate salts, thiobenzamide, N-substituted thiourea and thioacetate salts.

The present invention also provides a process for preparation of the compound of Formula (III), wherein the isoxazole of Formula (II) is reacted with a thionating reagent to yield a compound of the Formula (III):

Formula (III)

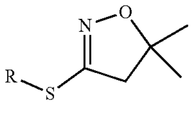

The present invention also provides an S-substituted thioisoxazole derivative of the general Formula (III):

Formula (III)

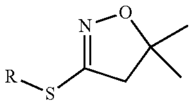

wherein R is acetyl, dithiooxamoyl, 1-(N,N-dimethylmethanaminium) salt, sulfonyl salt, alkoxycarbonyl and; 1-(1-phenylmethanone).

The present invention also provides a (5,5-dimethyl-4H-isoxazol-3-yl)benzenecarbimidothioate or a (5,5-dimethyl-4H-isoxazol-3-yl)benzenecarbimidothioate: wherein X is chloride, bromide, difluoromethanesulfinate and methanesulfinate.

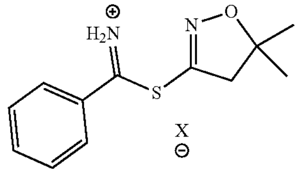

The present invention also provides a (5,5-dimethyl-4H-isoxazol-3-yl) 2-amino-2-thioxo-ethanimidothioate or (5,5-dimethyl-4H-isoxazol-3-yl) 2-amino-2-thioxo-ethanimidothioate:

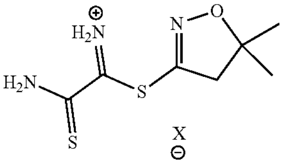

wherein X is chloride, bromide, difluoromethanesulfinate and methanesulfinate.

The present invention also provides a 5,5-dimethyl-3-sulfosulfanyl-4H-isoxazole sodium salt:

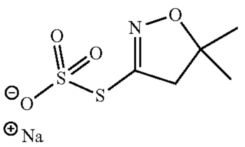

The present invention also provides a 2-(5,5-dimethyl-4H-isoxazol-3-yl)-1,3-dimethyl-isothiourea or 2-(5,5-dimethyl-4H-isoxazol-3-yl)-1,3-dimethyl-isothiourea:

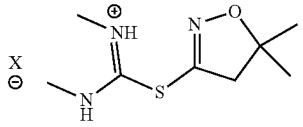

wherein X is chloride, bromide, difluoromethanesulfinate and methanesulfinate.

The present invention also provides a 2-(5,5-dimethyl-4H-isoxazol-3-yl)-1,3-diethyl-isothiourea or 2-(5,5-diethyl-4H-isoxazol-3-yl)-1,3-dimethyl-isothiourea:

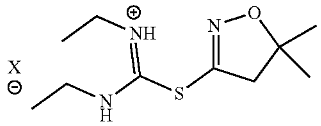

wherein X is chloride, bromide, difluoromethanesulfinate and methanesulfinate.

The present invention also provides a 3-(4,5-dihydro-1H-imidazol-2-ylsulfanyl)-5,5-dimethyl-4H-isoxazole or 3-(4,5-dihydro-1H-imidazol-2-ylsulfanyl)-5,5-dimethyl-4H-isoxazole:

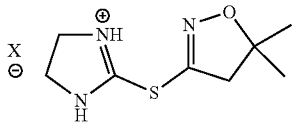

wherein X is chloride, bromide, difluoromethanesulfinate and methanesulfinate.

The present invention also provides an ethyl (5,5-dimethyl-4H-isoxazol-3-yl) sulfanylformate:

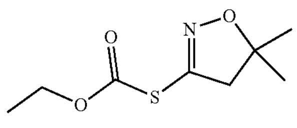

The present invention also provides an S-(5,5-dimethyl-4H-isoxazol-3-yl)ethanethioate:

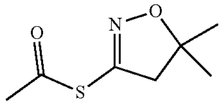

The present invention also provides a N,N-dimethyl (5,5-dimethyl-4H-isoxazol-3-ylsulfanyl)methaniminium or N,N-dimethyl (5,5-dimethyl-4H-isoxazol-3-ylsulfanyl)methaniminium:

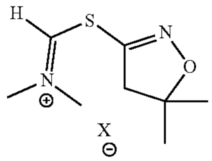

wherein X is chloride, bromide, difluoromethanesulfinate and methanesulfinate.

DESCRIPTION OF SPECIFIC EMBODIMENTS OF THE INVENTION

We have now found novel compounds which may be used as alternative intermediates in the synthetic pathway to prepare the compound of Formula (I); the novel synthetic pathway allows the synthesis of the compound of Formula (I) or analogs thereof without the isolation of a salt derived from the above-described prior art synthesis. Also, the novel intermediates can be isolated, and some are more stable towards hydrolysis. The use of N-substituted thioureas allows for less moisture sensitive salts to be prepared. Furthermore, non-salt derivatives where the isoxazoline of the general Formula (II) has a 3-substituent such as xanthyl, thio- and dithiocarboxyl or S-thiosulfonyl may be prepared. These S-substituted 2-isoxazoline-3-thiol derivates differ with respect to the synthesis of the compound of Formula (I) and its analogues in terms of the ease with which they release the corresponding 2-isoxazoline-3-thiolate upon base treatment. Improved yields of the compound of Formula (I) and its analogues may be obtained with slower generation of the active thiolate nucleophile in the reaction, as well as increasing operational simplicity in terms of addition rates. The provided processes represent environmentally-friendly alternatives to previously disclosed methods of preparation, reducing solvent waste and generating innocuous byproducts.

The sulfides of Formula (I) are synthetically accessible through a novel class of S-substituted thioisoxazole derivative the general Formula (III):

Formula (III)

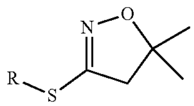

wherein R is acetyl, benzoyl, dithiooxamoyl, 1-(N,N-dimethylmethanaminium) salt, sulfonyl salt, alkoxycarbonyl, 1-(1-phenylmethanone) and; substituted thiourea.

Especially preferred are the S-substituted thioisoxazole derivatives of Formula (III) which are:

A (5,5-dimethyl-4H-isoxazol-3-yl)benzenecarbimidothioate or a (5,5-dimethyl-4H-isoxazol-3-yl)benzenecarbimidothioate:

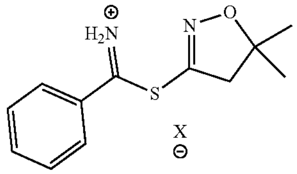

wherein X is chloride, bromide, difluoromethanesulfinate and methanesulfinate.

A (5,5-dimethyl-4-isoxazol-3-yl) 2-amino-2-thioxo-ethanimidothioate or (5,5-dimethyl-4H-isoxazol-3-yl) 2-amino-2-thioxo-ethanimidothioate:

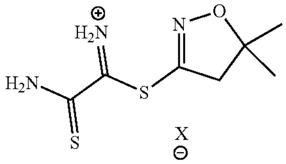

wherein X is chloride, bromide, difluoromethanesulfinate and methanesulfinate.

A 5,5-dimethyl-3-sulfosulfanyl-4H-isoxazole sodium salt:

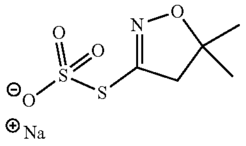

A 2-(5,5-dimethyl-4H-isoxazol-3-yl)-1,3-dimethyl-isothiourea or 2-(5,5-dimethyl-4H-isoxazol-3-yl)-1,3-dimethyl-isothiourea:

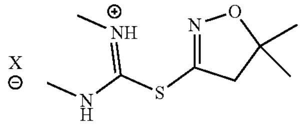

wherein X is chloride, bromide, difluoromethanesulfinate and methanesulfinate.

A 2-(5,5-dimethyl-4H-isoxazol-3-yl)-1,3-diethyl-isothiourea or 2-(5,5-diethyl-4H-isoxazol-3-yl)-1,3-dimethyl-isothiourea:

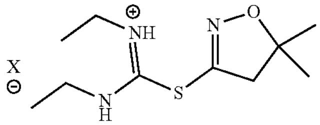

wherein X is chloride, bromide, difluoromethanesulfinate and methanesulfinate.

A 3-(4,5-dihydro-1H-imidazol-2-ylsulfanyl)-5,5-dimethyl-4H-isoxazole or 3-(4,5-dihydro-1H-imidazol-2-ylsulfanyl)-5,5-dimethyl-4H-isoxazole:

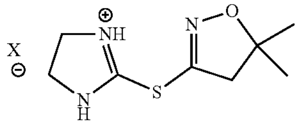

wherein X is chloride, bromide, difluoromethanesulfinate and methanesulfinate.

An ethyl (5,5-dimethyl-4H-isoxazol-3-yl)sulfanylformate:

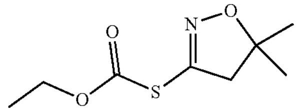

A S-(5,5-dimethyl-4H-isoxazol-3-yl)ethanethioate:

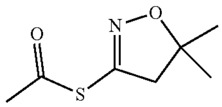

A N,N-dimethyl (5,5-dimethyl-4H-isoxazol-3-ylsulfanyl) methaniminium or N,N-dimethyl (5,5-dimethyl-4H-isoxazol-3-ylsulfanyl)methaniminium:

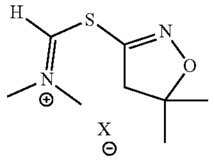

wherein X is chloride, bromide, difluoromethanesulfinate and methanesulfinate.

The synthetic pathway leading to the sulfide of Formula (I) is depicted below:

Scheme 1.

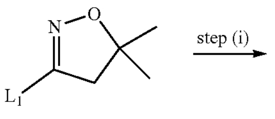

Formula (II)

-continued

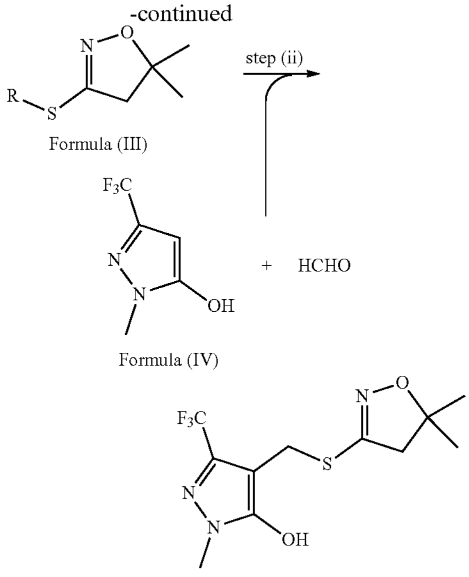

Formula (III)
Formula (IV)
Formula (I)

wherein:

$L_1$ is a leaving group; R is an organic residue derived from a suitable thionating reagent: dimethyl thioformamide, thiosulfate salts, dithiooxamide, alkyl xanthate salts, thiobenzamide, N-substituted thiourea and thioacetate salts.

In one aspect of the present invention is a process comprising the step of reacting an isoxazole of Formula (II) with a thionating reagent to create an S-substituted thioisoxazole of Formula (III).

In another aspect of the present invention is a process of combining the S-substituted thioisoxazole of Formula (III) with a pyrazole of the Formula (IV) by introducing a methylene bridge, to obtain a compound of Formula (I).

One approach towards S-substituting the isoxazole of the general Formula (II) involves its reaction with a thionating agent, which includes but is not limited to, potassium ethyl xanthate, dithiooxamide, thiobenzamide, potassium thioacetate, thiosulfate salt, dialkyl thioformamide and alkyl substituted thiourea in the presence of formaldehyde source, preferably in an alkaline environment.

Regarding the pyrazole of Formula (IV) starting material, it is commercially available, or can be prepared by methods known in the art, e.g., as described in WO 2004/013106 (≡EP 1541561), by the ring closure reaction of methyl hydrazine and 4,4,4-trifluoro-3-oxo-butyric acid ethyl ester. An illustrative procedure can be found in US 2013/015804 and U.S. Pat. No. 7,488,831.

Sources of formaldehyde include aqueous formaldehyde and paraformaldehyde. Paraformaldehyde (a polymer of the formula $HOCH_2(OCH_2)_{n-2}OCH_2OH$), gradually dissolves in alkaline environment, undergoing de-polymerization to give formaldehyde which participates in the reaction. For example, paraformaldehyde in a granular or prilled form with a degree of polymerization (n) in the range between $8<n<100$ may be utilized in the process. Another compound which can supply paraformaldehyde in-situ is 1,3,5-trioxane. A slight molar excess of formaldehyde in the reaction is usually beneficial, i.e., up to 3:1 relative to the pyrazole starting material.

An alkaline environment, even though not mandatory, greatly favors the reaction. Suitable bases for generating the alkaline environment in the reaction mixture include alkali metal hydroxides, alkali metal hydrogencarbonates, alkali metal alkoxides, alkali metals hydride, and where applicable the corresponding alkaline earth bases. The alkaline agents can be added to the reaction vessel either in a solid form, or as a concentrated aqueous solution. Organic bases, namely, pyridine derivatives and alkylamines can be used instead of the inorganic bases. The amount of the base is in the range of 2:1 to 10:1 relative to the pyrazole starting material.

The coupling reaction involving the use of the pyrazole of Formula (IV) with formaldehyde and the S-substituted thioisoxazole of Formula (III) takes place in water and/or in an organic solvent, i.e., protic solvents, polar aprotic solvents (including halogenated hydrocarbons) and aromatic solvents. Aqueous solvents, i.e., water alone and solvent mixtures consisting of water and water miscible organic solvent, particularly polar aprotic solvent, e.g., acetonitrile, dimethylformamide, dimethylsulfoxide and propylene carbonate were found to be useful. Other classes of organic solvents are also suitable, e.g., aqueous mixtures of lower alkanols or ethers. Such mixtures, e.g. water/acetonitrile, can also be used to supply the pyrazole of Formula (IV) to the reaction vessel in the form of a solution, to facilitate the feeding of the reactants to the reaction vessel. Thus, a suitably proportioned reaction medium consists of water/organic solvent at 9:1-1:9 weight ratio. Roughly equally proportioned solvent mixtures, or perhaps with slight water predominance, are usually preferred.

The reactants and reagents can be added in succession to the reaction vessel; simultaneous feeding of two or more reactants is also workable. No particular requirements are placed on the order of addition, with the exception that the pyrazole starting material is brought into contact with the formaldehyde source in the reaction vessel in an alkaline environment. Typically, the thionating reagent is added to the aforementioned reaction mixture derived from the pyrazole and formaldehyde reacting in an alkaline medium.

The mixture of thionating reagent and the isoxazole of the general Formula (II) or their analogues, for example 4,5-dihydroisoxazoles bearing a leaving group at the 3-position such as sulfonyl leaving groups, may be evaporated after a period which may be between an hour and 72 hours, typically 16 hours and triturated with a solvent such as an aliphatic or aromatic hydrocarbon, an ester or an ethereal solvent to allow for isolation of an intermediate reagent capable of releasing the conjugate base of a 2-isoxazoline-3-thiol upon base treatment, thus allowing this intermediate reagent to be used neat or in solution as a replacement for the mixture of thionating reagent and the isoxazole of the general Formula (II) or their analogues.

Different types of solvents can be utilized for the reaction, e.g., ethers (including cyclic ethers such as tetrahydrofuran and dioxane), aliphatic alcohols, halogenated hydrocarbons, and polar aprotic solvents such as dimethylformamide, and optionally aqueous mixtures thereof. The reaction is preferably carried out under inert gas atmosphere, optionally with heating.

In one aspect of the present invention the process for preparing a compound of Formula (I) further comprising the step of reacting the compound of the Formula (I) with a compound of the formula $F_2HC\text{-}L_1$, wherein $L_1$ is a leaving group, optionally followed by an oxidation step and thereby obtaining pyroxasulfone.

Formal displacement of $L_1$ in $F_2HC\text{-}L_1$ ($L_1$ is preferably chlorine or bromine, e.g. $F_2HC\text{-}L_1$ is chlorodifluoromethane) by the action of thioester of Formula (I) in strongly basic conditions can take place in different solvents (polar aprotic solvents, such as dimethylformamide, dimethylacetamide, acetonitrile and dimethyl sulfoxide are generally preferred) in the presence of a base (alkali metal hydroxides, alkali metal carbonates, alkali metal alkoxides, alkali metals hydrides, nitrogen-containing organic bases, namely, trialkyl amines and pyridine derivatives). The fluorinated methyl halide $F_2HC\text{-}L_1$ is used in stoichiometric excess. The amount of the base introduced to the reaction vessel is preferably from 1 to 5 equivalents to one equivalent of the thioester of Formula (I).

Lastly, the fluorinated-sulfide of Formula (I) analogue undergoes oxidation to give the herbicidally active compound, i.e., pyroxasulfone. The oxidation reaction is accomplished by methods known in the art, using oxidizing agents such as organic and inorganic peroxides; operative oxidizers include hydrogen peroxide, m-chloroperoxybenzoic acid, peroxyacetic acid, perbenzoic acid, magnesium monoperoxyphthalate, potassium peroxy monosulfate, potassium permanganate and sodium periodate. As an alternative to direct conversion of the sulfide functionality to sulfone-$SO_2$, one may consider an oxidation reaction passing through the corresponding sulfoxide (—SO), i.e., with isolation of the sulfoxide and subsequent oxidation to the sulfone. The oxidation can take place in water, in organic solvent and/or in any combinations of thereof. Organic solvents such as halogenated hydrocarbons (either halogenated aliphatic hydrocarbons such as dichloromethane and chloroform or halogenated aromatic hydrocarbons such as chlorobenzene); ethers such as dioxane, tetrahydrofuran (THF), and diethyl ether; $C_1$-$C_4$ alkanols; ketones; and amides can be used. The temperature during the oxidation may vary from 0° C. to 80° C., usually temperatures of 20° C. to 40° C. are preferred. Illustrative procedures can be found in WO 2004/013106 (≡EP 1541561).

Interestingly, the isoxazole of the general Formula (II) reacts in the same way with different leaving groups attached to the isoxazole. The sulfinylisoxazole:

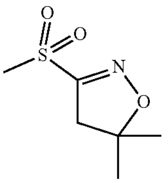

reacts in the same manner in subsequent reactions of the present invention as the halo-substituted isoxazole of the general Formula (II). For example, without any limitations to the present invention, the thionating reagent in this case is sodium methanethiolate ($Na^+$ $^-SMe$), then the product is oxidized and now the halogen, ‘X,’ has been replaced with methanesulfinite ($MeSO_2^-$). This leaving group is displaced by another thiol to give the product, as it may be illustrated in Scheme 2:

Scheme 2.

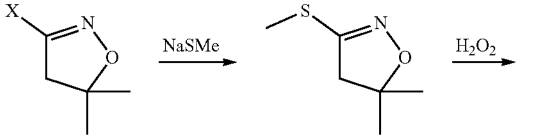

-continued

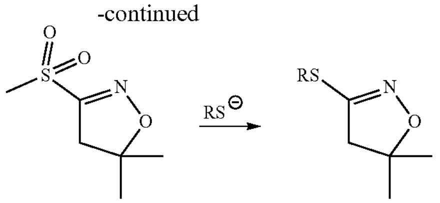

Methanesulfinite as a leaving group which makes the compound less moisture sensitive and therefore easier to handle in the reaction. The isoxazole with methanesulfinite can be prepared without using the halo-substituted isoxazole of the general Formula (II) as the starting material.

Definitions

Unless defined otherwise, all technical and scientific terms used herein have the meaning commonly understood by persons of ordinary skill in the art to which this subject matter pertains.

The term “alkyl” as used herein, refers to a branched, unbranched, or cyclic carbon chain, including methyl, ethyl, propyl, isopropyl, cyclopropyl and the like.

As used herein, the term “isoxazole” is 5,5-dimethyl-4H-isoxazole.

As used herein, the term “isoxazole of Formula (II)” is 5,5-dimethyl-4H-isoxazole bearing a leaving group at the 3-position or isoxazole bearing a leaving group at the 3-position if isoxazole is 5,5-dimethyl-4H-isoxazole.

As used herein, the term “S-substituted thioisoxazole” is 5,5-dimethyl-4H-isoxazole bearing a substituted sulfur atom at the 3-position.

As used herein, the term “thionating reagent” is a reagent capable of forming a new sulfur-carbon bond.

As used herein, the term “leaving group” is a molecular fragment that arises from heterolytic bond cleavage and which carries an electron pair from the bond broken during fragmentation.

In particular the leaving group may be but is not limited to, fluoroalkylsulfinates, alkylsulfonates, arylsulfonates, chloride and bromide.

As used herein, the term “stable” when used in connection with a composition means that the composition is physically stable and chemically stable. As used herein, the term “chemically stable” means that no significant decomposition of the active components was observed after at least 2 weeks of storage in a sealed package at a temperature of 54° C. As used herein, the term “physically stable” means that no significant sedimentation was observed after at least 2 weeks of storage in a sealed package at a temperature of 54° C.

The term “a” or “an” as used herein includes the singular and the plural, unless specifically stated otherwise. Therefore, the terms “a,” “an,” or “at least one” are used interchangeably in this application.

Throughout the application, descriptions of various embodiments are described using the term “comprising”; however, it will be understood by one of skill in the art, that in some specific instances, an embodiment can be described using the language “consisting essentially of” or “consisting of.”

The term “about” herein specifically includes ±10% from the indicated values in the range. In addition, the endpoints of all ranges directed to the same component or property herein are inclusive of the endpoints, are independently combinable, and include all intermediate points and ranges.

It is understood that where a parameter range is provided, all integers within that range, and tenths thereof, are also provided by the invention as if the integers and tenths thereof are expressly described herein. For example, "0.1% to 70%" includes 0.1%, 0.2%, 0.3%, 0.4%, 0.5% etc. up to 70%.

All publications, patents and patent applications mentioned in this specification are herein incorporated in their entirety by reference into the specification, to the same extent as if each individual publication, patent or patent application was specifically and individually indicated to be incorporated herein by reference.

The following examples illustrate the practice of the present subject matter in some of its embodiments but should not be construed as limiting the scope of the present subject matter. Other embodiments apparent to persons of ordinary skill in the art from consideration of the specification and examples herein that fall within the spirit and scope of the appended claims are part of this invention. The specification, including the examples, is intended to be exemplary only, without limiting the scope and spirit of the invention.

Aspects and embodiments of the present invention will now be described.

The present invention provides a process for preparing a compound of the Formula (I)

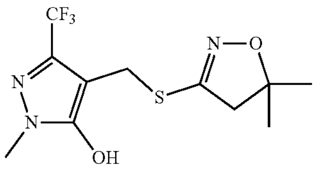

(I)

which comprises the following steps:

i) reacting an isoxazole of Formula (II) with a thionating reagent to create an S-substituted thioisoxazole of Formula (III);

ii) combining the S-substituted thioisoxazole of Formula (III) with a pyrazole of the Formula (IV) by introducing a methylene bridge, to obtain a compound of Formula (I)

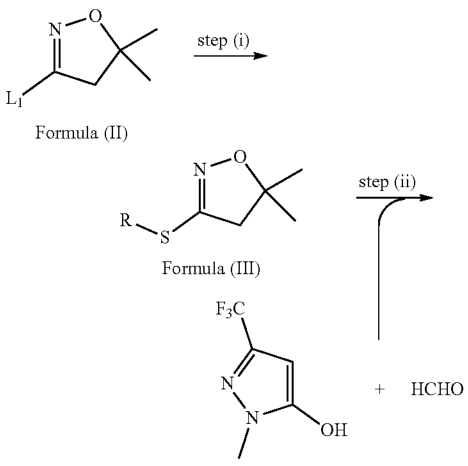

Formula (II)

Formula (III)

Formula (IV)

-continued

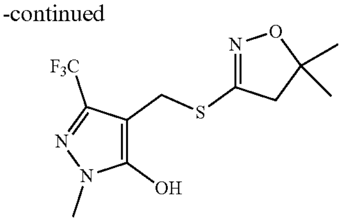

Formula (I)

wherein $L_1$ is a leaving group; R is an organic residue derived from a suitable thionating reagent: dimethyl thioformamide, thiosulfate salts, dithiooxamide, alkyl xanthate salts, thiobenzamide, N-substituted thiourea and thioacetate salts.

In some embodiments, a process according to claim 1, wherein the isoxazole of Formula (II) is sulfinylisoxazole

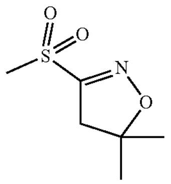

or halogen-substituted isoxazole:

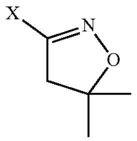

wherein X is halogen.

In some embodiments, a process for preparing a compound of the Formula (I) comprising reacting an isoxazole of Formula (II) with a thionating reagent to create an S-substituted thioisoxazole of Formula (III), followed by combining the S-substituted thioisoxazole of Formula (III) with a pyrazole of the Formula (IV) by introducing a methylene bridge, using an alkaline environment, to obtain a compound of Formula (I).

In some embodiments, a process for preparing a compound of the Formula (I) comprising reacting an isoxazole of Formula (II) with a thionating reagent to create an S-substituted thioisoxazole of Formula (III), followed by combining the S-substituted thioisoxazole of Formula (III) with a pyrazole of the Formula (IV) by introducing a methylene bridge, using a formaldehyde source, to obtain a compound of Formula (I).

In some embodiments, a process for preparing a compound of the Formula (I) comprising reacting an isoxazole of Formula (II) with a thionating reagent to create an S-substituted thioisoxazole of Formula (III), followed by combining the S-substituted thioisoxazole of Formula (III) with a pyrazole of the Formula (IV) by introducing a methylene bridge, using an acid, to obtain a compound of Formula (I).

In some additional embodiments, a process for preparing a compound of the Formula (I) comprising reacting an isoxazole of Formula (II) with a thionating reagent to create an S-substituted thioisoxazole of Formula (III), followed by combining the S-substituted thioisoxazole of Formula (III) with a pyrazole of the Formula (IV) by introducing a methylene bridge, to obtain a compound of Formula (I) with any combination of procedural synthetic conditions described herein.

In some embodiments a process comprising the isoxazole of Formula (II) which is reacted with a thionating reagent selected from a group comprising: potassium ethyl xanthate, dithiooxamide, thiobenzamide, potassium thioacetate, thiosulfate salt, dialkyl thioformamide and alkyl substituted thiourea to create an S-substituted thioisoxazole of Formula (III).

In some embodiments a process comprising an isoxazole of Formula (II) and the thionating reagent which are reacted in an organic polar aprotic solvent selected from a group comprising: acetonitrile, dimethylformamide, N-methyl-2-pyrrolidone, dimethyl sulfoxide, ethylene carbonate, propylene carbonate, dimethylacetamide, dichloromethane, dichloroethane and tetrahydrofuran.

In some embodiments a process comprising an isoxazole of Formula (II) and the thionating reagent which are reacted in at a temperature of −10° C. to 60° C.

In some embodiments a process comprising an isoxazole of Formula (II) and the thionating reagent which are reacted in at a temperature of 20° C. to 40° C.

In some embodiments a process comprising combining the S-substituted thioisoxazole of Formula (III) with a pyrazole of the Formula (IV) by introducing a methylene bridge in the presence of formaldehyde source in an alkaline environment.

In some embodiments the alkaline environment is a 2.5 M aqueous solution of an alkaline metal hydroxide and water.

In some embodiments a process comprising a formaldehyde source which is a 4.5 M formaldehyde solution in water or para-formaldehyde.

In some embodiments a process comprising charging a reaction vessel while stirring with the thionating reagent and the isoxazole of Formula (II) in an organic solvent, followed by the addition of this mixture to a mixture of formaldehyde and a pyrazole of the Formula (IV) in an alkaline environment.

In some embodiments a process for preparation of the compound of Formula (III), wherein the isoxazole of Formula (II) is reacted with a thionating reagent to yield a compound of the Formula (III):

Formula (III)

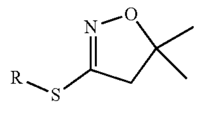

In some embodiments a process comprising the isoxazole of Formula (II) which is reacted with a thionating reagent to yield a compound of the Formula:

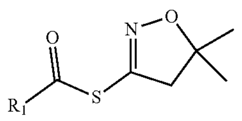

wherein $R_1$ is $C_1$-$C_3$ alkyl.

In some embodiments a process comprising the isoxazole of Formula (II) which is reacted with a thionating reagent to yield a compound of the Formula:

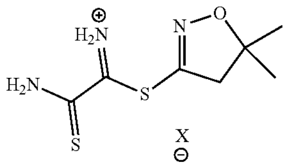

wherein X is a counter-anion.

In some embodiments a process comprising the isoxazole of Formula (II) which is reacted with a thionating reagent to yield a compound of the Formula:

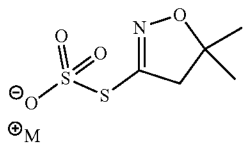

wherein M is a counter-cation

In some embodiments a process comprising the isoxazole of Formula (II) which is reacted with a thionating reagent to yield a compound of the Formula:

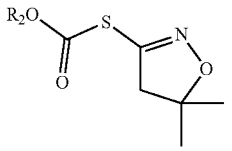

wherein $R^2$ is H, $C_1$-$C_3$ alkyl.

In some embodiments a process comprising the isoxazole of Formula (II) which is reacted with a thionating reagent to yield a compound of the Formula:

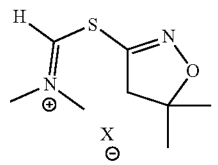

wherein X is a counter-anion.

In some embodiments a process comprising the isoxazole of Formula (II) which is reacted with a thionating reagent to yield a compound of the Formula:

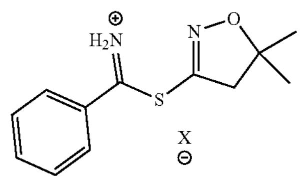

wherein X is a counter-anion.

In some embodiments a process comprising the isoxazole of Formula (II) which is reacted with a thionating reagent to yield a compound of the Formula:

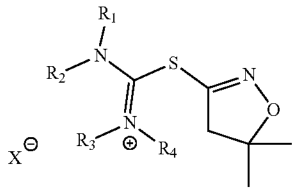

wherein X is a counter-anion; and $R_1$ is $C_1$-$C_3$ alkyl, $R_2$, $R_3$ and $R_4$ are H, alkyl.

In some embodiments a process comprising the isoxazole of Formula (II) which is reacted with a thionating reagent to yield a compound of the Formula:

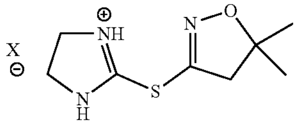

wherein X is a counter-anion.

In some embodiments, a process comprising the isoxazole of Formula (II) which is reacted with a thionating reagent in an organic solvent.

In some embodiments, a process comprising the isoxazole of Formula (II) which is reacted with a thionating reagent in an inert atmosphere.

In some embodiments, a process comprising the isoxazole of Formula (II) which is reacted with a thionating reagent at 0° C.

In some embodiments, a process comprising the isoxazole of Formula (II) which is reacted with a thionating reagent at room temperature.

In some embodiments, a process comprising the isoxazole of Formula (II) which is reacted with a thionating reagent with an addition of an acid.

In some embodiments, a process comprising the isoxazole of Formula (II) which is reacted with a thionating reagent in an organic solvent, in an inert atmosphere, at 0° C. to room temperature and with an addition of an acid.

In some additional embodiments, a process comprising the isoxazole of Formula (II) which is reacted with a thionating reagent with any combination of procedural synthetic conditions described herein.

In some embodiments the process further comprises the step of reacting the compound of the Formula (I) with a compound of the formula $F_2HC$-$L_1$, wherein $L_1$ is a leaving group, optionally followed by an oxidation step and thereby obtaining pyroxasulfone:

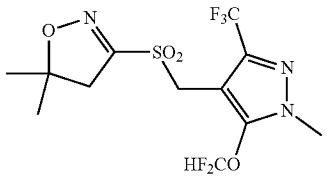

In another aspect of the present invention an S-substituted thioisoxazole the general Formula (III):

Formula (III)

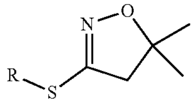

wherein R is acetyl, dithiooxamoyl, 1-(N,N-dimethylmethanaminium) salt, sulfonyl salt, alkoxycarbonyl and; 1-(1-phenylmethanone).

In another aspect of the present invention a (5,5-dimethyl-4H-isoxazol-3-yl)benzenecarbimidothioate or a (5,5-dimethyl-4H-isoxazol-3-yl)benzenecarbimidothioate: wherein X is chloride, bromide, difluoromethanesulfinate and methanesulfinate.

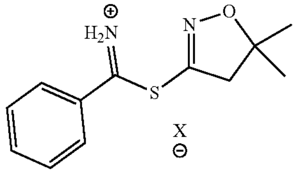

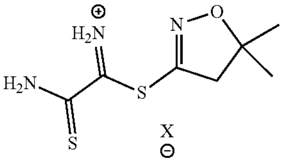

In yet another aspect of the present invention a (5,5-dimethyl-4H-isoxazol-3-yl) 2-amino-2-thioxo-ethanimidothioate or (5,5-dimethyl-4H-isoxazol-3-yl) 2-amino-2-thioxo-ethanimidothioate:

wherein X is chloride, bromide, difluoromethanesulfinate and methanesulfinate.

In yet another aspect of the present invention a 5,5-dimethyl-3-sulfosulfanyl-4H-isoxazole sodium salt:

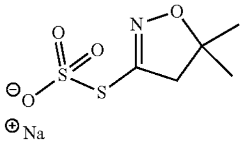

In yet another aspect of the present invention a 2-(5,5-dimethyl-4H-isoxazol-3-yl)-1,3-dimethyl-isothiourea or 2-(5,5-dimethyl-4H-isoxazol-3-yl)-1,3-dimethyl-isothiourea:

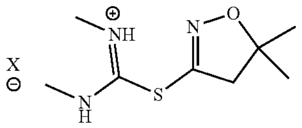

wherein X is chloride, bromide, difluoromethanesulfinate and methanesulfinate.

In still another aspect of the present invention a 2-(5,5-diethyl-4H-isoxazol-3-yl)-1,3-dimethyl-isothiourea or 2-(5,5-diethyl-4H-isoxazol-3-yl)-1,3-dimethyl-isothiourea:

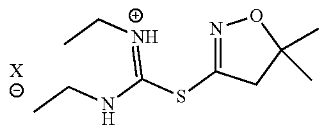

wherein X is chloride, bromide, difluoromethanesulfinate and methanesulfinate.

In yet another aspect of the present invention a 3-(4,5-dihydro-1H-imidazol-2-ylsulfanyl)-5,5-dimethyl-4-isoxazole or 3-(4,5-dihydro-1H-imidazol-2-ylsulfanyl)-5,5-dimethyl-4H-isoxazole:

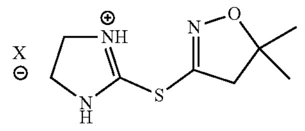

wherein X is chloride, bromide, difluoromethanesulfinate and methanesulfinate.

In still another aspect of the present invention an S-(5,5-dimethyl-4H-isoxazol-3-yl) ethanethioate:

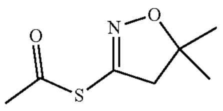

In still another aspect of the present invention an ethyl (5,5-dimethyl-4H-isoxazol-3-yl)sulfanylformate:

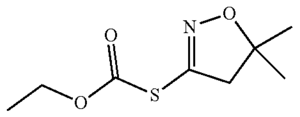

In another aspect of the present invention a N,N-dimethyl (5,5-dimethyl-4H-isoxazol-3- or N,N-dimethyl (5,5-dimethyl-4H-isoxazol-3-ylsulfanyl)methaniminium ylsulfanyl) methaniminium:

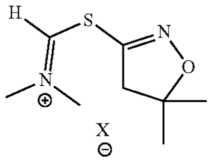

wherein X is chloride, bromide, difluoromethanesulfinate and methanesulfinate.

In some embodiments of the present invention the process for producing a compound of Formula (I) and novel intermediates of the general Formula (III), provides increased synthetic yields, slower generation of the active thiolate nucleophile in the reaction, as well as increasing operational simplicity in terms of addition rates.

Each embodiment disclosed herein is contemplated as being applicable to each of the other disclosed embodiments. Thus, all combinations of the various elements described herein are within the scope of the invention. In addition, the elements recited in process embodiments can be used in combination with compound embodiments described herein and vice versa.

This invention will be better understood by reference to the Examples which follow, but those skilled in the art will readily appreciate that the specific experiments detailed are only illustrative of the invention as described more fully in the claims which follow thereafter.

The invention is illustrated by the following examples without limiting it thereby.

EXAMPLES

NMR spectrum was recorded with Bruker 400 MHz spectrometer.

Melting point was determined by a Büchi B-545 melting point apparatus.

Example 1

Preparation of N,N-dimethyl (5,5-dimethyl-4H-isoxazol-3-ylsulfanyl)methaniminium Bromide

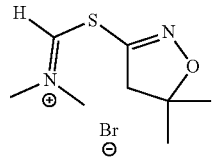

As described in Scheme 3: Dimethylthioformamide (2.0 g) and 3-bromo-5,5-dimethyl-2-isoxazoline (4.0 g) were taken up in MeCN (35 mL), under a nitrogen atmosphere, and the reaction mixture cooled to 0° C. Trifluoroacetic acid (0.13 mL) was added, and the reaction mixture stirred (4 h), allowing to warm to room temperature. Methyl tert-butyl ether (100 mL) was added over 5 minutes, with stirring, then stirring continued for 10 minutes. Filtration and washing of the solid with methyl tert-butyl ether (50 mL), followed by drying in vacuo gave the product as a light yellow powder (5.5 g, 92%); $^{1}$H NMR (400 MHZ, $CD_3CN$) 11.13 (1H, s), 3.84 (3H, s), 3.42 (3H, s), 3.51 (2H, s), 1.46 (6H, s), $^{13}$C NMR (100 MHz, $CD_3CN$) 179.45 (CH), 147.79 (C), 89.51 (C), 50.28 ($CH_2$), 49.51 ($CH_3$), 44.15 ($CH_3$), 27.28 ($2{\times}CH_3$).

Scheme 3.

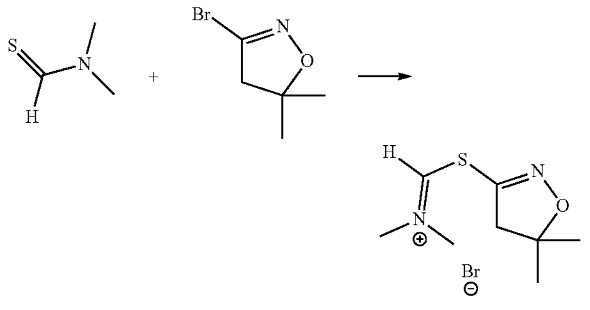

Example 2

Preparation of the compound of Formula (I) using N,N-dimethyl (5,5-dimethyl-4H-isoxazol-3-ylsulfanyl)methaniminium Chloride

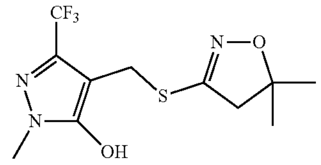

As described in Scheme 4: Dimethylthioformamide (7.06 g) and 3-bromo-5,5-dimethyl-2-isoxazoline (14.1 g) were taken up in MeCN (100 mL), under a nitrogen atmosphere, and the reaction mixture cooled to 0° C. Trifluoroacetic acid (0.30 mL) was added, and the reaction mixture stirred (4 h), allowing to warm to room temperature. 5-Hydroxy-1-methyl-3-(trifluoromethyl) pyrazole (13.2 g) was added in portions to a solution of NaOH (19 g) in water (200 mL), maintaining a temperature below 30° C. The mixture was cooled to 10° C. A solution of p-formaldehyde (4.76 g) and NaOH (2.0 g) in water (100 mL) was added with a syringe pump over 0.5 h, with stirring, at 10° C. The mixture was stirred for a further 30 minutes at 10° C. then the solution of dimethylthioformamide/bromoisoxazole adduct was added over 30 minutes at 10° C. The resulting mixture was stirred for a further 0.5 hours, allowing the temperature to rise to 15° C. then the pH adjusted to 1 with 4 M HCl, maintaining a temperature of 15° C., and the reaction stirred for a further half hour, whereupon the solid product was collected by filtration (18.95 g, 98.9% purity, 77% yield); $^1$H NMR (400 MHZ, $CDCl_3$) 10.33 (1H, s), 3.99 (2H, s), 3.68 (3H, s), 2.87 (2H, s), 1.43 (6H, s).

Scheme 4.

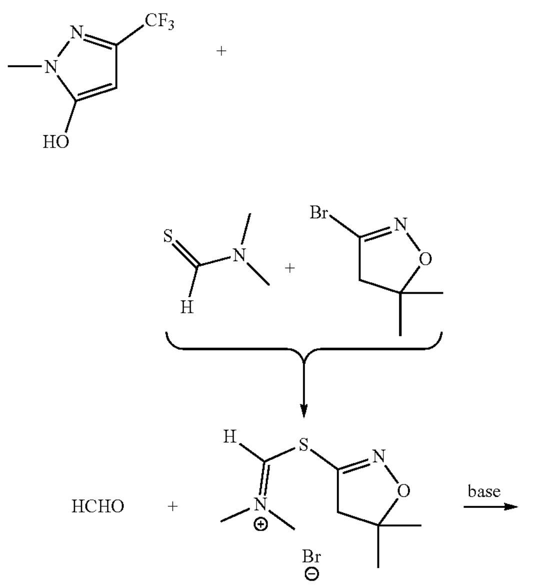

-continued

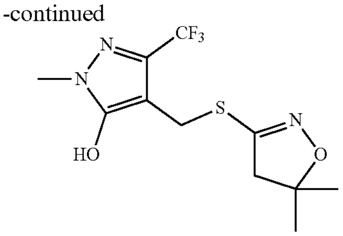

Example 3

Preparation of the Compound of Formula (I) Using N,N-dimethyl (5,5-dimethyl-4H-isoxazol-3-ylsulfanyl)methaniminium Chloride Formed at Elevated Temperature

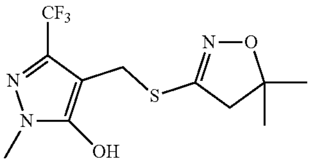

As described in Scheme 4: Dimethylthioformamide (12.60 g) and 3-bromo-5,5-dimethyl-2-isoxazoline (24.86 g, 91% assay) were taken up in MeCN (165 mL), under a nitrogen atmosphere, and the reaction mixture heated to 40° C. Trifluoroacetic acid (0.50 mL) was added, and the reaction mixture stirred (1-2 h), at 40° C. 5-Hydroxy-1-methyl-3-(trifluoromethyl) pyrazole (21.21 g) was added to a solution of NaOH (20.44 g) in water (200 mL), maintaining a temperature of 35° C. Solid p-formaldehyde (6.07 g) was added, with stirring, maintaining a temperature of 35° C. Water (180 mL) was added and the solution cooled to 10-15° C., then the solution of dimethylthioformamide/bromoisoxazole adduct was added over 20 minutes at 15° C. The resulting mixture was stirred for a further 0.5 hours, allowing the temperature to rise to 15° C. then the pH adjusted to 1 with 30% HCl, maintaining a temperature of 15° C., and the reaction cooled to 10° C. and stirred for a further half hour, whereupon the solid product was collected by filtration (31.26 g, 98.2% chromatographic purity, 98.0% assay, 78% yield).

Example 4

Preparation of 2-(5,5-dimethyl-4H-isoxazol-3-yl)-1,3-dimethyl-isothiourea Hydrochloride

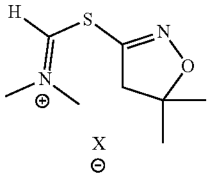

N,N'-Dimethylthiourea (2.0 g, 19 mmol, 1.0 equiv.) and 3-chloro-5,5-dimethyl-2-isoxazoline (2.6 g, 19 mmol, 1.0 equiv.) were stirred in MeCN (50 mL) for 2 days, following which the solvent was removed at 35° C. and the residue triturated with ethyl acetate (10 mL). The mixture was stirred (10 min) at room temperature then filtered and dried in vacuo to give colourless crystals of N,N'-dimethylcarbamimidothioic acid, 4,5-dihydro-5,5-dimethyl-3-isoxazolyl ester hydrochloride (3.9 g, 96%).

Example 5

Preparation of the Compound of Formula (I) Using 2-(5,5-dimethyl-4H-isoxazol-3-yl)-1,3-dimethyl-isothiourea Hydrochloride

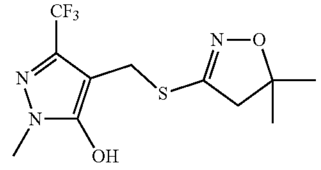

As described in Scheme 5: To a solution of NaOH (0.89 g, 22 mmol, 4.0 equiv.) in water (6 mL) was added 5-hydroxy-1-methyl-3-(trifluoromethyl) pyrazole (0.91 g, 5.5 mmol, 1.0 equiv). Over 30 minutes an aqueous formaldehyde solution (37%, methanol stabilised, 0.80 mL, 11 mmol, 2.0 equiv.) was added. After a further hour of stirring a solution of N,N'-dimethylcarbamimidothioic acid, 4,5-dihydro-5,5-dimethyl-3-isoxazolyl ester hydrochloride (1.3 g, 5.5 mmol, 1.0 equiv.) in water (5 mL) was added over 5 minutes. After stirring for a further hour the pH was adjusted to 1 by gradual addition of 4 M HCl, stirred for a further 15 minutes and filtered then dried in vacuo to give 4-[[(4,5-dihydro-5,5-dimethyl-3-isoxazolyl)thio]methyl]-1-methyl-3-(trifluoromethyl)-1H-pyrazol-5-ol (1.65 g, 92% purity, 89%).

Scheme 5.

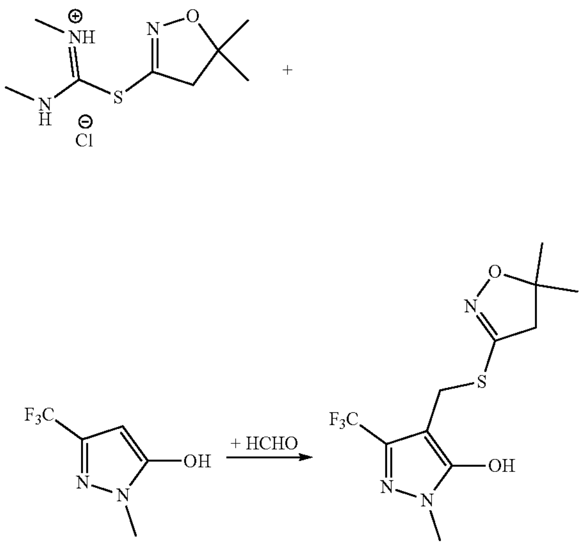

Example 6

Preparation of the Compound of Formula (I) Using a Compound of the General Formula (III)—General Procedure

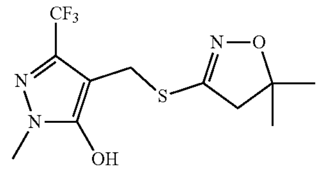

To a solution of NaOH (4.0 equiv.) in water (about 6 mL) is added 5-hydroxy-1-methyl-3-(trifluoromethyl) pyrazole (1.0 equiv). For between 15 minutes to 2 hours a formaldehyde source solution (2.0 equiv.) is added. After an additional between 30 minutes to 3 hours of stirring a solution of a thionating reagent, a compound of the general Formula (III) (1.0 equiv.) in water (5 mL) is added gradually. After stirring for a further between 30 minutes to 3 hours the pH is adjusted to 1 by gradual addition of an acid, stirring for a further between 5 minutes to 30 minutes and filtering, then drying in vacuo, yielding 4-[[(4,5-dihydro-5,5-dimethyl-3-isoxazolyl)thio]methyl]-1-methyl-3-(trifluoromethyl)-1H-pyrazol-5-ol (between 80% to 99% purity, between 70% to 99% yield).

In addition, any priority document(s) of this application is/are hereby incorporated herein by reference in its/their entirety.

What is claimed is:

1. An S-substituted thioisoxazole derivative the general Formula (III):

Formula (III)

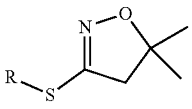

wherein R is acetyl, dithiooxamoyl, 1-(N,N-dimethylmethanaminium) salt, sulfonyl salt, alkoxycarbonyl, 1-(1-phenylmethiminium), or being (5,5-dimethyl-4H-isoxazol-3-yl) benzenecarboximidothioate or a (5,5-dimethyl-4H-isoxazol-3-yl) benzenecarboximidothioate of:

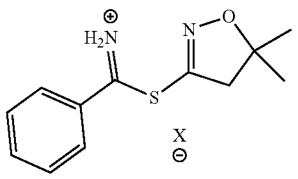

wherein X is chloride, bromide, difluoromethanesulfinate or methanesulfinate, or (5,5-dimethyl-4H-isoxazol-3-yl) 2-amino-2-thioxo-ethanimidothioate or (5,5-dimethyl-4H-isoxazol-3-yl) 2-amino-2-thioxo-ethanimidothioate of:

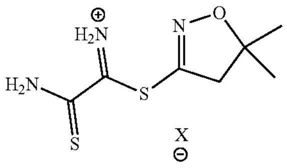

wherein X is chloride, bromide, difluoromethanesulfinate and methanesulfinate, or 5,5-dimethyl-3-sulfosulfanyl-4H-isoxazole sodium salt:

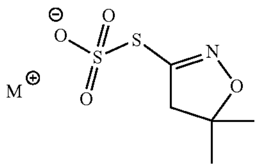

or 2-(5,5-dimethyl-4H-isoxazol-3-yl)-1,3-dimethyl-isothiourea or 2-(5,5-dimethyl-4H-isoxazol-3-yl)-1,3-dimethyl-isothiourea of:

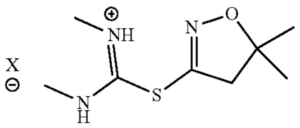

wherein X is chloride, bromide, difluoromethanesulfinate and methanesulfinate, or 2-(5,5-diethyl-4H-isoxazol-3-yl)-1,3-dimethyl-isothiourea or 2-(5,5-diethyl-4H-isoxazol-3-yl)-1,3-dimethyl-isothiourea of:

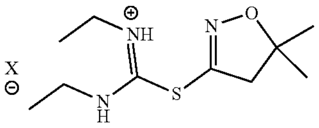

wherein X is chloride, bromide, difluoromethanesulfinate and methanesulfinate, or 3-(4,5-dihydro-1H-imidazol-2-ylsulfanyl)-5,5-dimethyl-4H-isoxazole or 3-(4,5-dihydro-1H-imidazol-2-ylsulfanyl)-5,5-dimethyl-4H-isoxazole of:

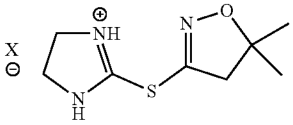

wherein X is chloride, bromide, difluoromethanesulfinate or methanesulfinate, or ethyl (5,5-dimethyl-4H-isoxazol-3-yl)sulfanylformate of:

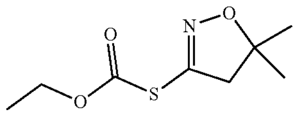

or S-(5,5-dimethyl-4H-isoxazol-3-yl) ethanethioate of:

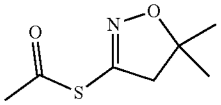

or N,N-dimethyl(5,5-dimethyl-4H-isoxazol-3-ylsulfanyl) methaniminium or N,N-dimethyl(5,5-dimethyl-4H-isoxazol-3-ylsulfanyl)methaniminium of:

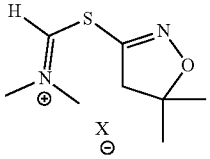

wherein X is chloride, bromide, difluoromethanesulfinate or methanesulfinate.

* * * * *